US00PP11417P

United States Patent [19]

Trees

[11] Patent Number: Plant 11,417

[45] Date of Patent: Jun. 13, 2000

[54] GERANIUM PLANT NAMED 'BFP-1568'

[75] Inventor: Scott C. Trees, Nipomo, Calif.

[73] Assignee: Ball Floraplant a division of Ball Horticultural Co., West Chicago, Ill.

[21] Appl. No.: 09/114,058

[22] Filed: Jul. 10, 1998

[51] Int. Cl.[7] ..... A01H 5/00

[52] U.S. Cl. ..... Plt./330

[58] Field of Search ..... Plt./325, 327, 330, Plt./329

[56] References Cited

U.S. PATENT DOCUMENTS

P.P. 9,560 5/1996 Trees ..... Plt./327

P.P. 9,774 12/1996 Utecht ..... Plt./330

*Primary Examiner*—Howard J. Locker

*Assistant Examiner*—Kent L. Bell

*Attorney, Agent, or Firm*—C. A. Whealy

[57] ABSTRACT

A new and distinct cultivar of Geranium plant named 'BFP-1568', characterized by its numerous semi-double coral orange-colored flowers; upright and rounded growth habit; vigorous and basal branching; and medium green leaves with a distinct zonation pattern.

1 Drawing Sheet

BACKGROUND OF THE INVENTION

The present invention relates to a new and distinct cultivar of Geranium plant, botanically known as *Pelargonium×hortorum*, and hereinafter referred to by the cultivar name 'BFP-1568'.

The new Geranium is a product of a planned breeding program conducted by the Inventor in Arroyo Grande, Calif. The objective of the breeding program was to develop new cultivars with excellent basal branching, medium growth habit, numerous flowers and umbels, and interesting flower and foliage colors.

The new Geranium originated from a cross made by the Inventor of the proprietary *Pelargonium×hortorum* selection 6583-52 as the male, or pollen parent, with the proprietary *Pelargonium×hortorum* selection 6702-55 as the female, or seed parent. The cultivar 'BFP-1568' was discovered and selected by the Inventor as a flowering plant within the progeny of the stated cross in a controlled environment in Arroyo Grande, Calif., on Sep. 15, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'BFP-1568'. These characteristics in combination distinguish 'BFP-1568' as a new and distinct cultivar:

1. Numerous semi-double coral orange-colored flowers.
2. Upright and rounded growth habit.
3. Vigorous and basal branching.
4. Medium green leaves with a distinct zonation pattern.

The new Geranium can be compared to the cultivar, 'Designer Coral' (disclosed in U.S. Plant Pat. No. 8,522). However, in side-by-side comparisons conducted by the Inventor in Arroyo Grande, Calif., plants of the new Geranium differ from plants of the cultivar 'Designer Coral' in the following characteristics:

1. Plants of the new Geranium have smaller leaves than plants of the cultivar 'Designer Coral'.
2. Plants of the new Geranium have more flowers per umbel than plants of the cultivar 'Designer Coral'.
3. Flower color of plants of the new Geranium is darker and more intense than flower color of plants of the cultivar 'Designer Coral'.

A detailed comparison of plants of the cultivar 'BFP-1568' and the cultivar 'Designer Coral' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in a colored reproduction of this type. The photograph comprises a top perspective view of a typical plant of 'BFP-1568'. Flower and foliage colors in the photograph may appear different from the actual colors due to light refectance.

DETAILED BOTANICAL DESCRIPTION

The cultivar 'BFP-1568' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Pelargonium×hortorum* cultivar BFP-1568.

Parentage:

*Male parent.*—Proprietary *Pelargonium×hortorum* selection 6583-52.

*Female parent.*—Proprietary *Pelargonium×hortorum* selection 6702-55.

Propagation:

*Type cutting.*—Terminal cuttings.

*Time to initiate roots.*—About 7 days at temperatures about 18° C.

*Time to develop roots.*—about 21 days at temperatures about 18° C.

*Rooting habit.*—Fibrous and freely branching.

Plant description:

*General appearance.*—Upright and rounded growth habit, vigorous. Appropriate for 10 and 12.5-cm containers. About nine weeks are required to produced a finished 10-cm container from a rooted cutting.

*Growth and branching habit.*—Basally branching with about two lateral branches at the base.

*Plant height, base of plant to top of leaf plane.*—About 29 cm.

*Plant width.*—About 21.3 cm.

*Lateral branches.*—Length: About 13 cm. Internode length: About 3.3 cm. Color: 145B.

*Foliage description.*—Leaves simple, generally symmetrical, abundant, opposite. Quantity of leaves per lateral branch: About 12. Length: About 5.5 cm. Width: About 9 cm. Shape: Reniform with rounded apex, cordate base, and crenate margin. Texture: Leathery, both surfaces pubescent. Color: Fully expanded foliage, upper surface: 137B with zonation pattern, 139A in color, about 2.4 cm wide. Fully expanded foliage, lower surface: 137C. Venation, upper surface: 145A. Venation, lower surface: 146D. Petiole: Length: About 6 cm. Diameter: About 3.5 mm. Color: 145B.

Flower description:

*Flower type and habit.*—Coral orange-colored flowers. Very freely and continuously flowering. Flowers arranged in spherical umbels arising from apical leaf axils. Umbels displayed above or beyond the foliage. Usually about five umbels per plant. Flowers semi-double and round. Umbels persistent.

*Flowering season.*—Year-round under greenhouse conditions. In the garden, flowering is continuous from spring through summer.

*Umbels.*—Number of flowers per umbel: About 40. Diameter: About 10.1 cm. Height: About 8 cm.

*Flowers.*—Diameter: About 4.7 cm. Depth (height): About 1.5 cm.

*Flower buds.*—Length: About 1.2 cm. Diameter: About 7 mm. Shape: Elliptic.

*Petals.*—Quantity: Five, overlapping. Usually about three petaloids per flower. Length: About 3.1 cm. Width: About 2.4 cm. Shape: Obovate with rounded apex and entire margin. Texture: Smooth. Color: Fully opened, upper surface: 43A, to 44B/45B. Fully opened, lower surface: 43B. Petaloids: Irregular in shape with very narrow base; about 1.7 cm in length and about 2 mm in width; lower third of petaloids are white, 155D, upper portions are 43A in color.

*Peduncle* (*umbel stem*).—Length: About 20.5 cm. Strength: Strong. Angle: Mostly erect. Texture: Pubescent. Color: 144A.

*Pedicel* (*individual flower stem*).—Length: About 3 cm. Strength: Strong. Angle: Upright or outward. Texture: Pubescent. Color: 143C overlaid with 181A becoming more predominately red, 181A, with age.

*Reproductive organs.*—Androecium: Anther size: About 2 mm. Amount of pollen: Moderate. Pollen color: 31A. Gynoecium: Ovary color: Green.

Disease resistance: Under commercial conditions, resistance to pathogens has not been observed.

Seed development: Seed production has not been observed.

CHART A

| CHARACTERISTIC | 'BFP-1568' | 'DESIGNER CORAL' |
|---|---|---|
| PLANT HEIGHT | About 29 cm | About 28 cm |
| PLANT WIDTH | About 21.3 cm | About 20.8 cm |
| INTERNODE LENGTH | About 3.3 cm | About 4 cm |
| LEAF LENGTH | About 5.5 cm | About 6.4 cm |
| LEAF WIDTH | About 9 cm | About 10.8 cm |
| UMBEL DIAMETER | About 10.1 cm | About 11.3 cm |
| UMBEL HEIGHT | About 8 cm | About 6.8 cm |
| NUMBER OF FLOWERS PER UMBEL | About 40 | About 31 |
| PETAL COLOR, UPPER SURFACE | 43A to 44B/45B | 41A to 39A/41B |
| PETAL COLOR, LOWER SURFACE | 43B | 41C |
| PEDUNCLE LENGTH | About 20.5 cm | About 21.8 cm |

It is claimed:

1. A new and distinct cultivar of Geranium plant named 'BFP-1568', as illustrated and described.

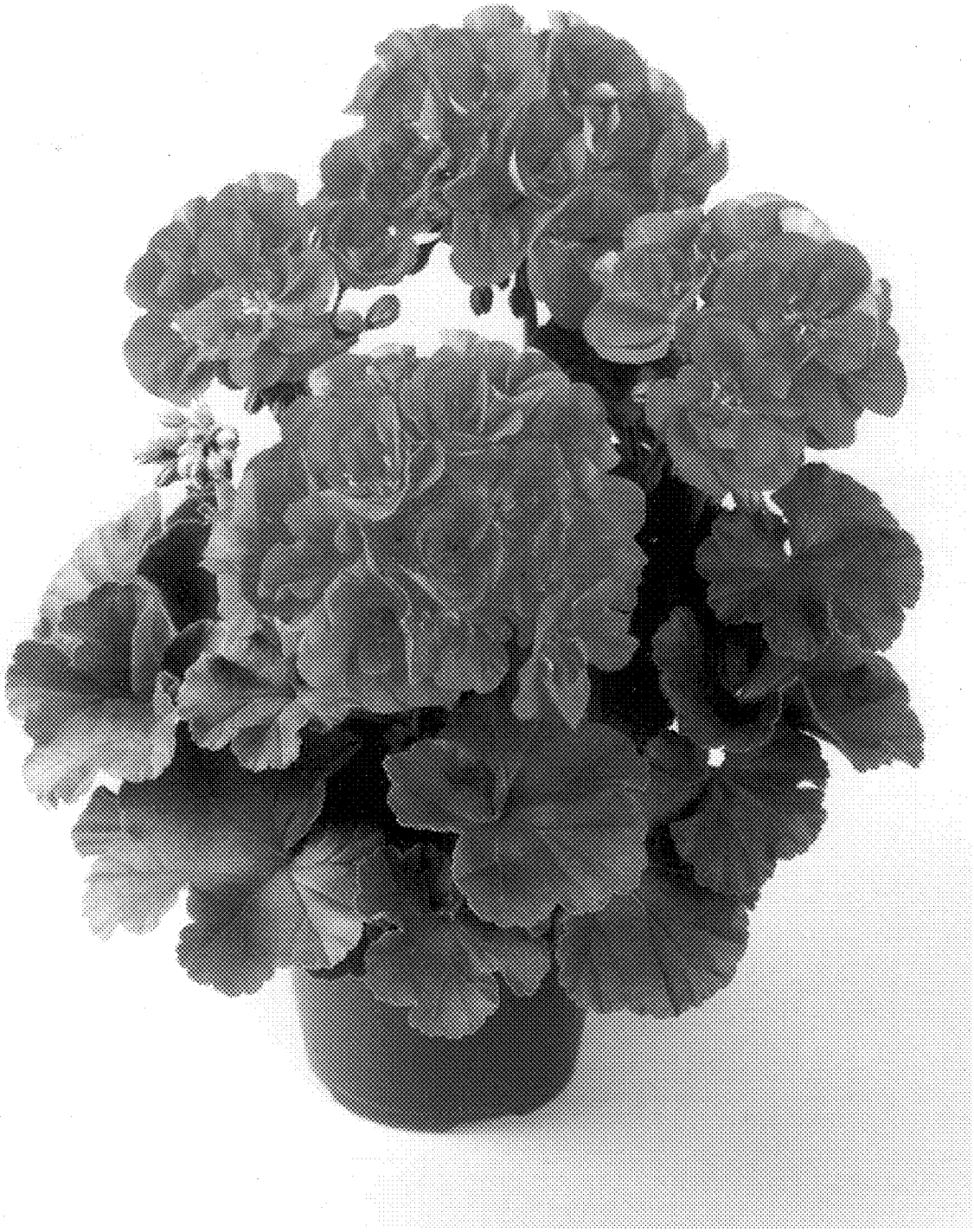

* * * * *